United States Patent [19]

Jelley et al.

[11] Patent Number: 5,317,897
[45] Date of Patent: Jun. 7, 1994

[54] METHOD FOR DETECTING THE PRESENCE OF A GAS WITH AN OPTO-ELECTRONIC GAS SENSOR

[75] Inventors: Kevin W. Jelley, Allentown, N.J.; G. Jordan Maclay, Maywood, Ill.

[73] Assignee: Siemens Corporate Research, Inc., Princeton, N.J.

[21] Appl. No.: 983,982

[22] Filed: Nov. 30, 1992

Related U.S. Application Data

[62] Division of Ser. No. 458,032, Dec. 28, 1989, Pat. No. 5,191,784.

[51] Int. Cl.$^5$ .................... G01N 21/00; G01N 33/00
[52] U.S. Cl. .................... 73/31.06; 73/31.01; 257/21; 257/414; 356/437; 436/144
[58] Field of Search ............ 436/144; 73/31.01, 31.05, 73/31.06; 356/437; 257/21, 15, 414

[56] References Cited

U.S. PATENT DOCUMENTS

| | | | |
|---|---|---|---|
| 3,479,257 | 11/1969 | Shaver | 436/144 |
| 4,348,686 | 9/1982 | Esaki et al. | 257/21 |
| 4,521,800 | 6/1985 | Howe | 257/755 |
| 4,581,621 | 4/1986 | Reed | 257/20 |
| 4,620,214 | 10/1986 | Margalif et al. | 257/21 |
| 4,731,338 | 3/1988 | Ralston et al. | 437/22 |
| 4,745,452 | 5/1988 | Sollner | 257/25 |
| 4,819,036 | 4/1989 | Kuroda et al. | 257/22 |
| 4,833,511 | 5/1989 | Sugimoto | 257/21 |
| 4,836,012 | 6/1989 | Doty et al. | 73/31.06 |
| 4,863,245 | 9/1989 | Roxlo | 257/16 |
| 5,107,307 | 4/1992 | Onose et al. | 257/15 |
| 5,107,316 | 4/1992 | Jelley et al. | 257/432 |

FOREIGN PATENT DOCUMENTS

0275150  7/1988  European Pat. Off. .

OTHER PUBLICATIONS

"Tiny Electronic 'Noses' Promise Speedy Sensing", New York Times, Tuesday, Dec. 6, 1988.
"Quantum Well Makes New, High-Performance Optical Modulators", Thomas H. Wood, Laser Focus, Dec. 1986, pp. 121–124.
"Photocurrent response of GaInAs/InP multiple quantum well detectors . . . ", Temkin et al., Appl. Phys. Lett. 47(9), Nov. 1, 1985, pp. 978–980.
"A Dual mechanism Solid-State Carbon-Monoxide and Hydrogen Sensor . . . ", Jelley et al., IEEE Transactions on Electron Devices, vol. ED-34, No. 10, Oct. 1987, pp. 2086–2097.
"Well size related limitations on maximum electroabsorption in GaAs/AlGaAs . . . ", Jelley et al., Appl. Phys. Lett. 55(1), Jul. 3, 1989, pp. 70–72.
"High-speed optical modulation with GaAs/GaAlAs quantum wells in a p-i-n diode structure", Wood et al., Appl. Phys. Lett. 44(1), Jan. 1, 1984, pp. 16–18.
"Experimental Determination of Electroabsorption in GaAs/Al$_{0.32}$Ga$_{0.68}$As Multiple Quantum Well Structures . . . ", Jelley et al., Electronics Letter, Dec. 8, 1988, vol. 24, No. 25, pp. 1555–1557.
"High-contrast reflection modulation at normal incidence in asymmetric . . . ", Whitehead et al., Electronics Letters, Apr. 27, 1989, vol. 25, No. 9, pp. 566–568.

Primary Examiner—Robert J. Warden
Assistant Examiner—L. M. Crawford
Attorney, Agent, or Firm—Adel A. Ahmed

[57] ABSTRACT

Apparatus for detecting the presence of a gas in an ambient atmosphere comprises a multiple quantum well structure; a thin mesh of a transition metal formed on the multiple quantum well structure; and an arrangement for monitoring transmission of electromagnetic radiation through the mesh and the multiple quantum well structure.

3 Claims, 1 Drawing Sheet

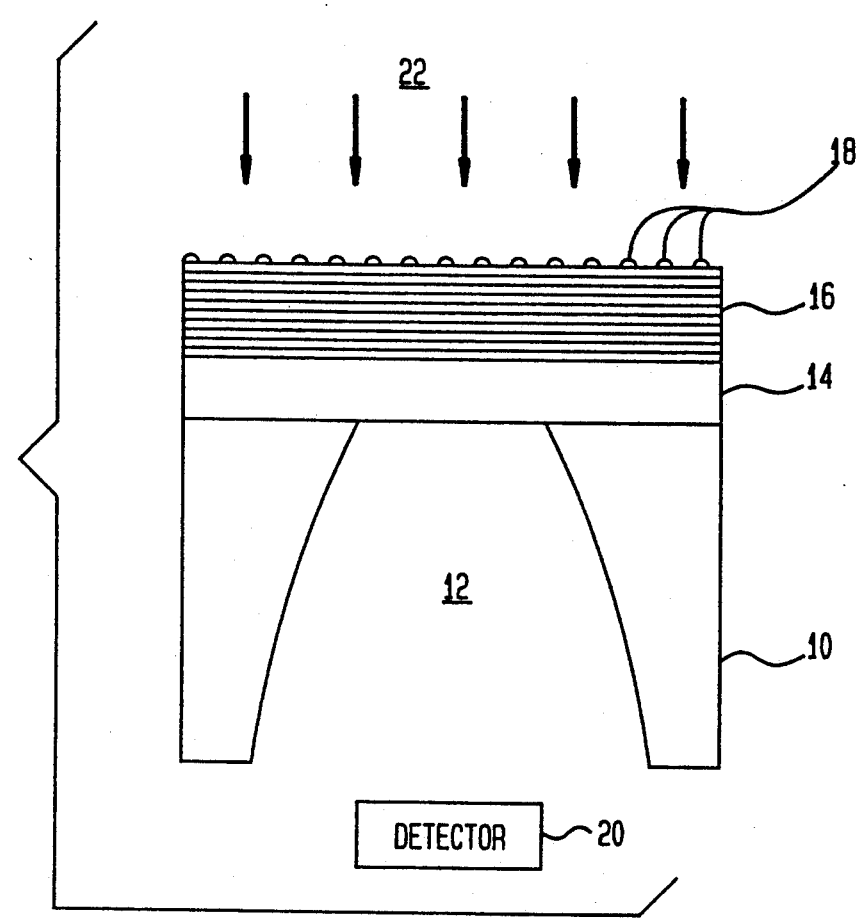
FIG. 1
FIG. 2
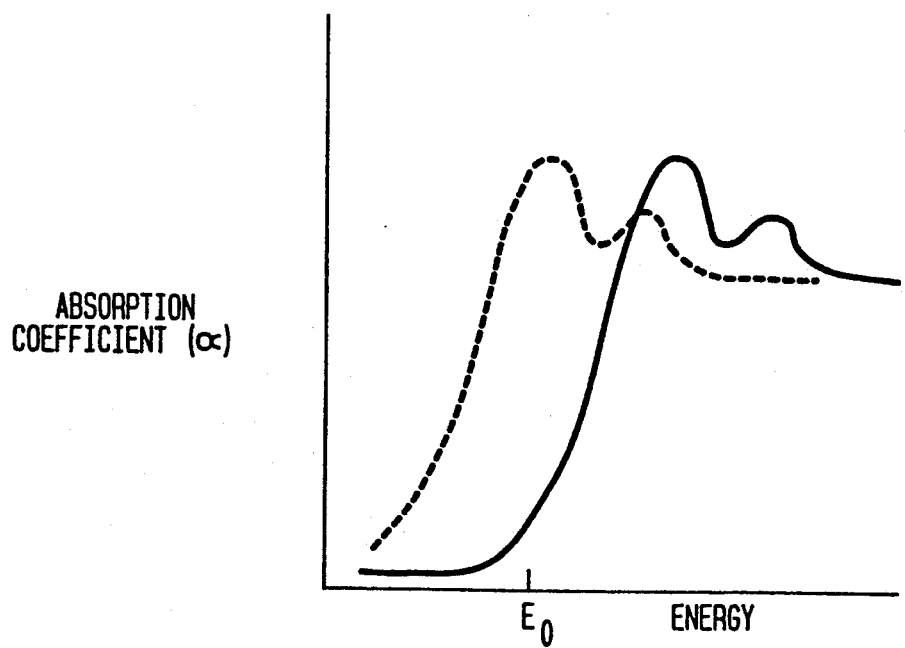
ABSORPTION COEFFICIENT ($\alpha$)
$E_0$   ENERGY

METHOD FOR DETECTING THE PRESENCE OF
A GAS WITH AN OPTO-ELECTRONIC GAS
SENSOR

This is a divisional, of application Ser. No. 07/458,032 filed Dec. 28, 1989, now U.S. Pat. No. 5,191,784.

The present invention relates to sensors for gases and, more particularly, to semiconductor sensors for sensing the presence of particular gases in the ambient atmosphere, such as a hydrogen component gas.

Sensors are known for detecting and signalling the presence of a gas by the effect of the gas on a semiconductor device. For example, a palladium-gate (Pd-gate) metal-oxide-semiconductor (MOS) structure sensitive to hydrogen gas is known. Such devices include a gate made of a transition metal, typically palladium in place of the conventional gate material generally utilized for an MOS device gate, such as aluminum or polysilicon. In a gas sensing device, the role of such a palladium gate structure is two-fold.

First, the gate acts as an electrode in contacting the device, and second, when exposed to hydrogen gas ($H_2$), gas, the palladium gate surface acts as a catalyst in the dissociation of molecular hydrogen into atomic hydrogen, which is then adsorbed on the Pd surface. Some of the atomic hydrogen will diffuse through the bulk palladium and be adsorbed at the interface of the palladium and the silicon, dioxide ($SiO_2$), layer which typically is deposited under the gate electrode. The adsorbed hydrogen both at the surface and at the interface is polarized and forms a dipole layer. The dipole layer at the interface causes a shift in the threshold voltage ($V_T$) of the MOS structure. The magnitude of the threshold shift due to the dipole layer is approximately proportional to the density of dipoles at the interface, which in turn is related to the concentration of hydrogen in the gas. It is also believed that a change in bulk hydrogen concentration also causes a shift in the work function, which will shift the threshold voltage.

Other gases such as hydrogen sulfide and ammonia have been sensed with a Pd-gate MOS structure. Gases such as carbon monoxide are adsorbed on the palladium surface but are too large molecularly to diffuse through the palladium bulk and therefore, give no response. Response to carbon monoxide has been obtained using a modified Pd gate in which holes from 1.5 to 3.0 μm in diameter have been patterned through the palladium to permit the carbon monoxide to reach the palladium-silicon dioxide interface.

In a further development, an ultra-thin palladium film has been deposited as an array of small individual islands separated from each other by a distance on the order of a few Å to about 100Å. The thickness of the film is kept below the point at which the islands tend to merge and, typically, may be in the order of 25Å. Electrical contact between the individual island globules occurs as a result of electron tunnelling. An account of the foregoing technology is provided, for example, in the article "A Dual-Mechanism Solid-State Carbon-Monoxide and Hydrogen Sensor Utilizing and Ultrathin Layer of Palladium", by Kevin W. Jelley and G. Jordan Maclay, IEEE Transactions on Electron Devices, Vol. ED-34, No. 10; October 1987.

Sensing of the shift in threshold voltage of the MOS device is typically performed by conventional electrical circuit arrangements. However, this requires connections to the MOS device, generally to the source and drain electrodes. It is herein recognized that the need for supply and sensing connections is a disadvantage, for example, in applications in which a sensor is located such that access has to be provided through gas-tight walls or glass windows. In accordance with an aspect of the invention, apparatus for detecting the presence of a gas in an ambient atmosphere comprises a multiple quantum well structure or superlattice; a thin mesh of a transition metal formed on the multiple quantum well structure; and an arrangement for monitoring transmission of electromagnetic radiation through the mesh and the multiple quantum well structure.

In accordance with another aspect of the invention, a semiconductor device adapted for operation as a gas sensor comprises a body of a semiconductor material including a substrate region and including a multiple quantum well region over the substrate region. The superlattice region has first and second different materials arranged alternately in a plurality of parallel planar layers. The planar layers exhibit an absorption edge for electromagnetic radiation at a first wavelength thereof and have a respective predetermined relatively thin thickness dimension of a value wherein an electric field acting perpendicularly to the planar layers causes the absorption edge to shift to a second wavelength of the electromagnetic radiation. A layer of a transition metal is formed over the superlattice region, the layer of transition metal having a relatively thin thickness dimension. The substrate region has at least a portion thereof removed for providing a clear passage for the electromagnetic radiation.

In accordance with still another aspect of the invention, the layer of transition metal is sufficiently thin as to be substantially transparent to the electromagnetic radiation.

In accordance with yet another aspect of the invention, the layer of transition metal is sufficiently thin as to be substantially permeable to a gas.

In accordance with a further aspect of the invention, the first material is aluminum gallium arsenide ($Al_x$-$GaAs_{1-x}$) and the second material is gallium arsenide (GaAs).

In accordance with yet a further aspect of the invention, the layer of transition metal is of palladium.

In accordance with still a further aspect of the invention, the layer of a transition metal is formed on a single layer of the superlattice region, the final layer being of aluminum gallium aresenide.

BRIEF DESCRIPTION OF THE DRAWINGS

The invention will next be described in greater detail by way o an exemplatory embodiment and with the aid of the drawing in which FIG. 1 shows an embodiment of the invention, not to scale; and FIG. 2 is a graph, helpful in understanding the invention.

Referring to FIG. 1, a gallium aresenide substrate 10 is doped at a level in the order of $10^{20}$ cm$^3$. Substrate 10 is opaque to electromagnetic radiation in the wavelength range of interest which is in the vicinity of 850 nanometers. Accordingly, a portion of substrate 10 is removed by etching so as to leave free a passage, generally indicated by reference numeral 12, around the center axis open of free passage of electromagnetic radiation, including light rays. Substrate 10 has formed thereon a region 14 of AlGaAs doped slightly less than the substrate, $10^{18}$ cm$^{-3}$. An undoped multiquantum well structure (MQW) 16 is formed over region 14. MQW 16 comprises a plurality of alternating layers of GaAs and AlGaAs, the layers being each in the order of 100 Å thick. A thin layer of a transition metal which may be palladium is formed over the topmost layer of MQW 16. Preferrably, this topmost layer of MQW 16 is of AlGaAs, although this is not essential. The thickness of the layer of palladium is preferably in the order of 50 Å. It is herein recognized that a palladium layer of such thin dimensions is typically discontinuous and on a microscopic scale comprises a mesh, masoic, or matrix-like spread of individual islands. The layer of palladium is thus indicated schematically in FIG. 1 as a series of dots 18. A light detector 20 is located in the clear path provided through the substrate so as to detect any light that is transmitted from a source above layer 18 through layer 18 and region 12. Light or other electromagnetic radiation incident on layer 18 is schematically shown in FIG. 1 as a series of arrows 22 emanating from a source not shown.

The characteristics of multiple quantum well structures such as MQW 16 are known. See the above referenced paper and, for example, the technical articles "Well size related limitations on maximum eletroabsorption in GaAsAlGaAs multiple quantum well structures", K. W. Jelley et al., Appl. Phys. Lett. 55(1), 3 Jul. 1989; pp 70-72; "High-speed optical modulation with GaAs/AlGaAs quantum wells in a p-i-n diode structure", T. H. Wood et al., Appl. Phys. Lett. 44(1), 1 Jan. 1984; "Experimental determination of electroabsorption in GaAs/Al$_{0.32}$Ga$_{0.68}$As multiple quantum well structures as functrion of well width", K. W. Jelley et al., Electronics Letters, 8th Dec. 1988, Vol. 24 No. 25 pp 1555-1557; ¢High-contrast reflection modulation at normal incidence in asymmetric multiple quantum well Fabry-Perot structure", M. Whitehead et al., Electronics Letters, 27th Apr. 1989, Vol. 25 No. 9, pp 566-568; and U.S. Pat. No. 4,731,338 (Ralston et al.), herein incorporated by reference.

Briefly, it is known that GaAs/AlGaAs quantum wells experience a shift to longer wavelengths in their absorption edge when acted upon by a perpendicular electric field. This is indicated schematically in FIG. 2 in which the solid line indicates the absorption coefficient without the presence of an electric field and the dashed line indicates the absorption coefficient under the action of an electric field. From FIG. 2 it is apparent that the absorption coefficient $\alpha$ for both the solid and dashed characteristics exhibits a region of sharp increase with increasing energy level. This sharp increase is conveniently referred to as an "absorption edge" and for the solid characteristic, it is shown in FIG. 2 as beginning at an energy level indicated as $E_0$.

In operation, light is transmitted through the structure, as described so as to impinge on detector 20. A wavelength somewhat longer than 850 nanometers is selected so as to be passed by the GaAs well whose absorption edge is at about 850 nanometers. Palladium layer 18 is then exposed to an atmosphere in which hydrogen may be present which it is desired to detect.

As has been earlier mentioned, it is known that when exposed to hydrogen gas (H$_2$), gas, the palladium surface acts as a catalyst in the dissociation of molecular hydrogen into atomic hydrogen, which is then adsorbed on the Pd surface. Some of the atomic hydrogen will diffuse through the interstices in the palladium mesh and be adsorbed at the surface of the topmost layer of MQW 16. The adsorbed hydrogen at the surface is polarized and forms a dipole layer. The dipole layer at the surface results in the effect of a bias being applied to palladium layer 18, which causes an electric field to act on MQW 16. The high level of doping in layer 14 and in substrate 10 will tend to restrict the resulting electric field to MQW 16 and thus maximize its effect. The electric field then causes the absorption edge to shift to a longer wavelength, as indicated in FIG. 2.

If the transmitted light being monitored is of the correct wavelength, it will now fall within the shifted absorption edge and detector 20 will register a drop in intensity and thereby indicate the presence of hydrogen. Naturally, the greater the concentration of hydrogen in the atmosphere to which the layer 18 is exposed, the greater the shift, so that the extent to which light is absorbed or transmitted provides a quantitative measure of the concentration of hydrogen in the ambient atmosphere.

The invention has been described by way of an illustrative embodiment. Various changes are possible which will be apparent to one skilled in the art. For example, other materials can be used for the detection of other gases and to allow operation at other wavelengths. For another example, light can be transmitted in either direction for monitoring of the absorption edge change. Such and similar changes and modifications do not depart from the spirit and scope of the invention which is intended to be limited only by the claims following.

We claim:

1. A method for detecting the presence of a gas in an ambient atmosphere comprising the steps of:
    transmitting electromagnetic radiation through a multiple quantum well structure and a thin mesh of a transition metal formed thereon;
    exposing said mesh to an ambient atmosphere containing a gas to be detected;
    monitoring detecting the presence of a gas by electromagnetic radiation transmitted through sa multiple quantum well structure and said thin mesh for a change.

2. A method as recited in claim 1, wherein said gas is hydrogen and said transition metal is palladium.

3. A method as recited in claim 2, wherein said change results from a shift of an absorption edge in said multiple quantum well structure.

* * * * *